United States Patent [19]

Ishii

[11] Patent Number: 4,527,551
[45] Date of Patent: Jul. 9, 1985

[54] CONNECTOR DEVICE FOR CHECKING LEAKAGE IN AN AIRTIGHT ENDOSCOPE

[75] Inventor: Fumiaki Ishii, Tokyo, Japan

[73] Assignee: Olympus Optical Co., Ltd., Tokyo, Japan

[21] Appl. No.: 514,313

[22] Filed: Jul. 15, 1983

[30] Foreign Application Priority Data

| Jul. 27, 1982 | [JP] | Japan | 57-113548[U] |
| Jul. 27, 1982 | [JP] | Japan | 113549[U] |
| Jul. 27, 1982 | [JP] | Japan | 57-113550[U] |
| Jul. 27, 1982 | [JP] | Japan | 113551[U] |
| Jul. 27, 1982 | [JP] | Japan | 57-113552[U] |

[51] Int. Cl.³ .............................................. A61B 1/00
[52] U.S. Cl. ...................................... 128/4; 251/149.5
[58] Field of Search ........................................ 128/4–8; 251/149.9, 149.5, 149.6

[56] References Cited

U.S. PATENT DOCUMENTS

| 2,305,841 | 12/1942 | Carlson | 251/149.6 |
| 2,727,759 | 12/1955 | Elliott | 251/149.6 |
| 3,809,122 | 5/1974 | Berg | 251/149.9 |
| 3,850,162 | 11/1974 | Iglesias | 128/6 |
| 3,960,139 | 6/1976 | Bailey | 604/190 |
| 4,216,767 | 8/1980 | Aoshiro | 128/4 |

Primary Examiner—Edward M. Coven
Assistant Examiner—Max F. Hindenburg
Attorney, Agent, or Firm—Frishauf, Holtz, Goodman & Woodward

[57] ABSTRACT

A connector device connects an airtight endoscope with an air supply line for use in a system for checking the endoscope for leakage, by feeding air into the body of the endoscope. The endoscope has a retaining member and a communication port including a valve mechanism for opening and closing the passage of the port. A connector of the air supply line is connected airtight to the passage of the port. The connector is provided with a retaining mechanism which is adapted to removably engage the retaining member located close to the port, thereby holding the air supply line connector.

8 Claims, 13 Drawing Figures

CONNECTOR DEVICE FOR CHECKING LEAKAGE IN AN AIRTIGHT ENDOSCOPE

BACKGROUND OF THE INVENTION

This invention relates to a connector device used in a system for checking an airtight endoscope for leakage, and more specifically to a connector device adapted to feed air into the body of an endoscope to check for leakage.

In general, various sections of an endoscope are subject to contamination, including an operating section and a universal cord coupled thereto, as well as an insertion section to be inserted into the body cavity in use. Accordingly, the whole body of the endoscope is made airtight, and is washed in water and then immersed in a disinfectant. If the sheath of the flexible insertion section or the sheath of the universal cord being washed and immersed for disinfection has any pinholes or cracks, the washing water and disinfectant will flow into the endoscope body to damage the optical system and other elements, possibly causing a serious accident.

Thus, the endoscope may be checked for leakage in the following manner. First, a communication portion is attached to, for example, the operating section of the endoscope to connect the inside and outside of the endoscope. Then, gas is supplied to the interior of the endoscope through the communication portion and pressurized. The endoscope is then immersed in water, and the presence or absence of gas leaking from the endoscope into the water is readily detected. In this case, however, the gas supply to the interior of the endoscope body should be achieved by the use of a mouthpiece attached to the end of a hose which is connected to a compressed air source. The mouthpiece is connected to the communication portion by press fitting with the aid of an O ring which is fitted on the inner peripheral surface of the mouthpiece. Accordingly, if external force is unexpectedly applied to the endoscope or hose during the leakage check, the mouthpiece will easily be disconnected from the communication portion.

To avoid this, the mouthpiece may be screwed into the communication portion. In this case, however, the attachment and detachment of the mouthpiece will require time, lowering the operating efficiency of the endoscope.

SUMMARY OF THE INVENTION

The object of this invention is to provide a connector device for checking an airtight endoscope for leakage, in which a supply connector for supplying gas to the interior of the airtight body of the endoscope through a port in the endoscope body can easily be attached to and detached from the port without the danger of unexpected disengagement.

According to this invention, there is provided a connector device used in a system for checking an air-leakage of an airtight endoscope, comprising an endoscope having an airtight endoscope body, a port formed in the endoscope body and having a passage communicated with the inside and outside space of the endoscope body, a valve mechanism for opening and closing the passage of the port, an operating mechanism for operating the valve mechanism, and a retaining member provided in the vicinity of the port, a supply connector connected with the passage of the port in an airtight manner, a supply line for supplying air for detecting air-leakage of the endoscope body through the supply connector and the passage of the port into the inside space of the endoscope body, and a retaining mechanism attached to the supply connector and adapted to engage the retaining member thereby removably holding the supply connector.

DETAILED DESCRIPTION OF THE PREFERRED EMBODIMENT

FIGS. 1 to 8 show a first embodiment of this invention.

Figure 1:
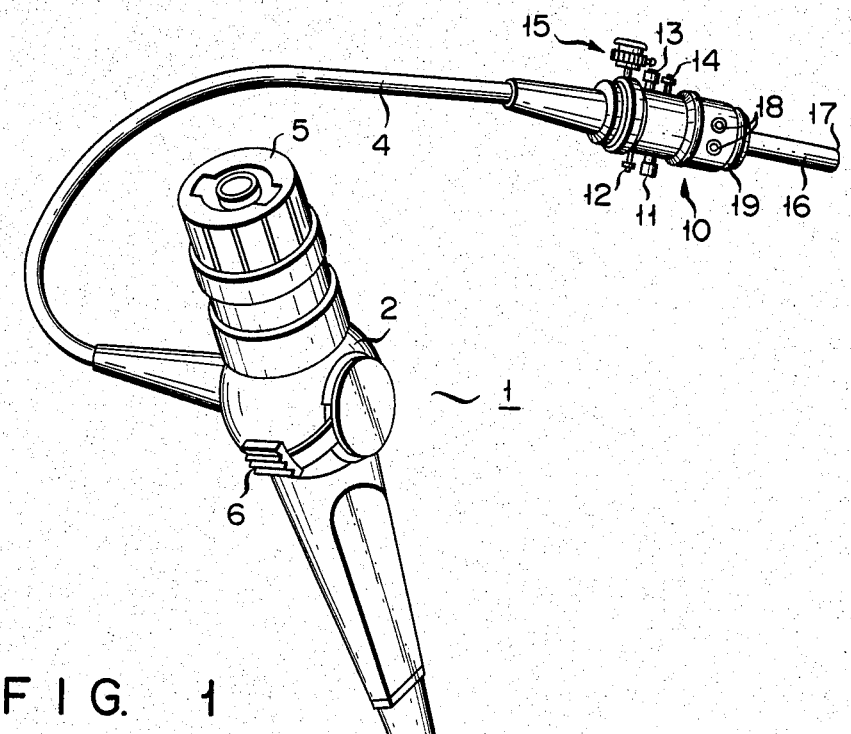
FIG. 1 is a perspective view of an airtight endoscope according to a first embodiment of this invention.

FIG. 1 shows an endoscope 1 with an airtight body. The endoscope 1 comprises an operating section 2, an insertion section 3 formed of an elongate flexible tube coupled to the operating section 2, and a universal cord 4. The operating section 2 is provided with an eyepiece portion 5, a bended operating knob 6, and selector valves (not shown) for air and water supply and suction. The insertion section 3 consists of a flexible tube portion 7, a bended tube portion 8, and a distal end portion 9. The insertion section 3 is adapted to be inserted into a body cavity. A connector 10 connected to a light source unit (not shown) is attached to the extended end of the universal cord 4. The connector 10 is provided, on the outer peripheral surface thereof, with an air/water mouthpiece 11, a $CO_2$ mouthpiece 12, a suction mouthpiece 13, an earth terminal 14, and a communication portion (a port) 15 to be described later. A light guide mouthpiece pipe 16 protrudes from the distal end face of the connector 10 and is inserted in a connecting socket of the light source unit. The distal end edge of the light guide mouthpiece pipe 16 forms a rounded portion 17 facilitating the insertion into the connecting socket. Contact pins 18 and a retaining ring 19 are also provided on the connector.

Figure 2:
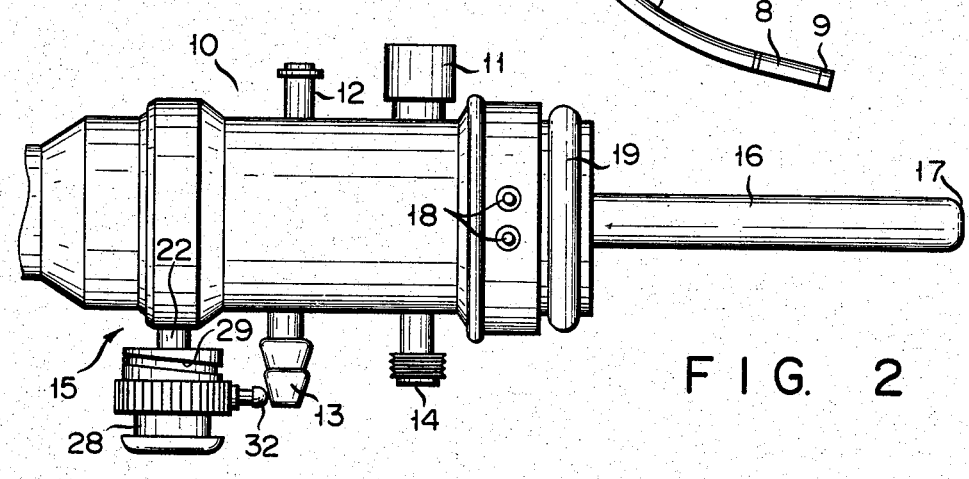
FIG. 2 is a side view of a connector attached to the extreme end of a universal cord of the endoscope.

The communication portion 15 is located in the vicinity of the suction mouthpiece 13 as shown in FIG. 2 and is constructed as shown in FIGS. 3 to 6. A mounting hole 21 is bored through a wall 20 of the connector 10. One end portion of a communication pipe 22 passes through the mounting hole 21. A first O ring 23 is interposed between the one end portion of the communication pipe 22 and the mounting hole 21. A nut-shaped fixing screw 24 is fitted on the outer periphery of the projected end portion of the communication pipe 22 inside the connector 10. The fixing screw 24 clamps and fixes the communication pipe 22 to the wall 20. A plate-like porous member 25 is held against the fixing screw 24 by a junk ring 26. The porous member 25 closes the open end portion of the communication pipe 22 from the inside of the endoscope 1. The porous member 25 is formed of, for example, polytetrafluoroethylene which, although impervious to water, is permeable to air, having pores of approximately 10 microns in diameter.

Figure 3:
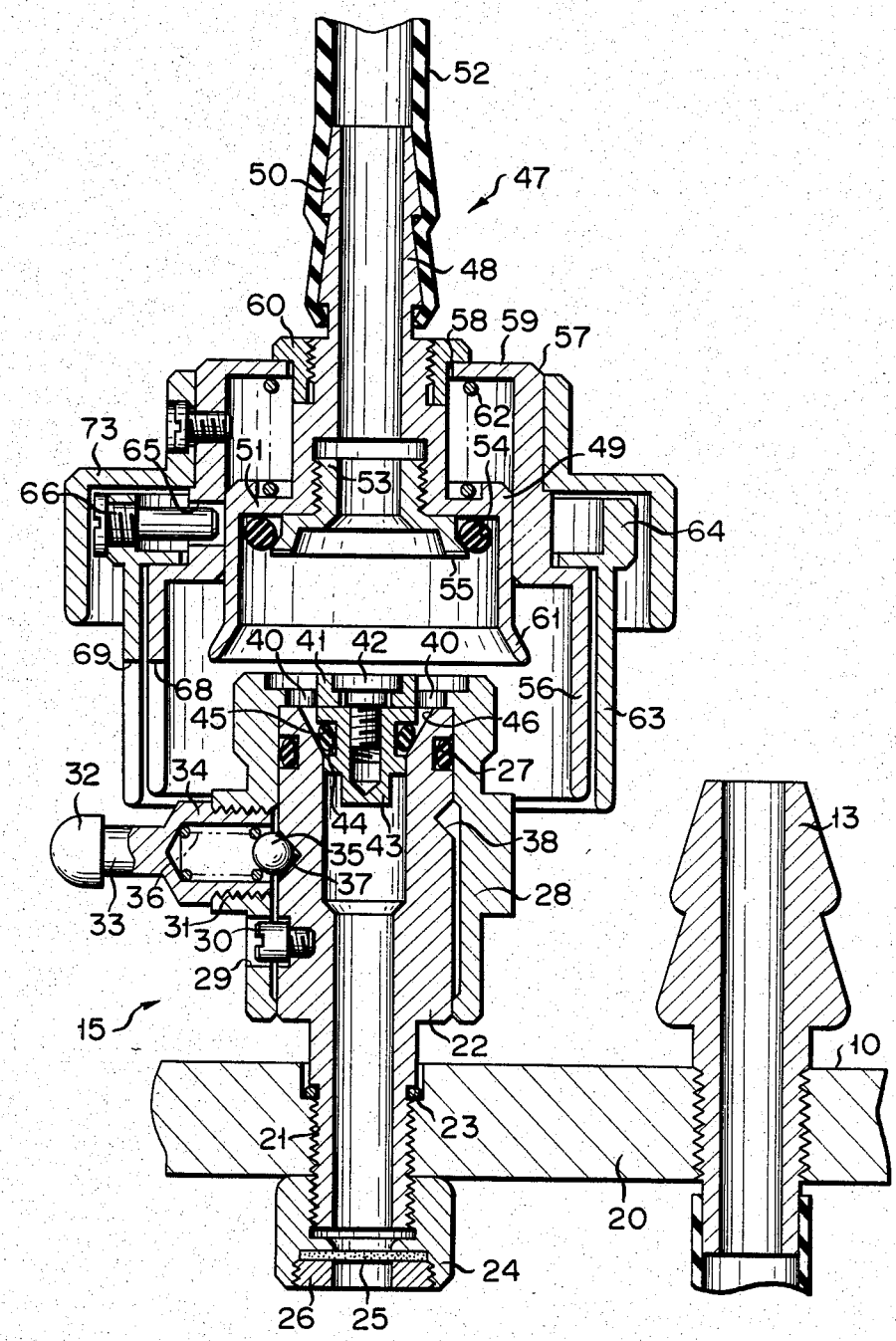
FIG. 3 is a side sectional view showing a communication portion according to the first embodiment and an air supply connector to be connected thereto in a state such that they are separated from each other.
Figure 5:
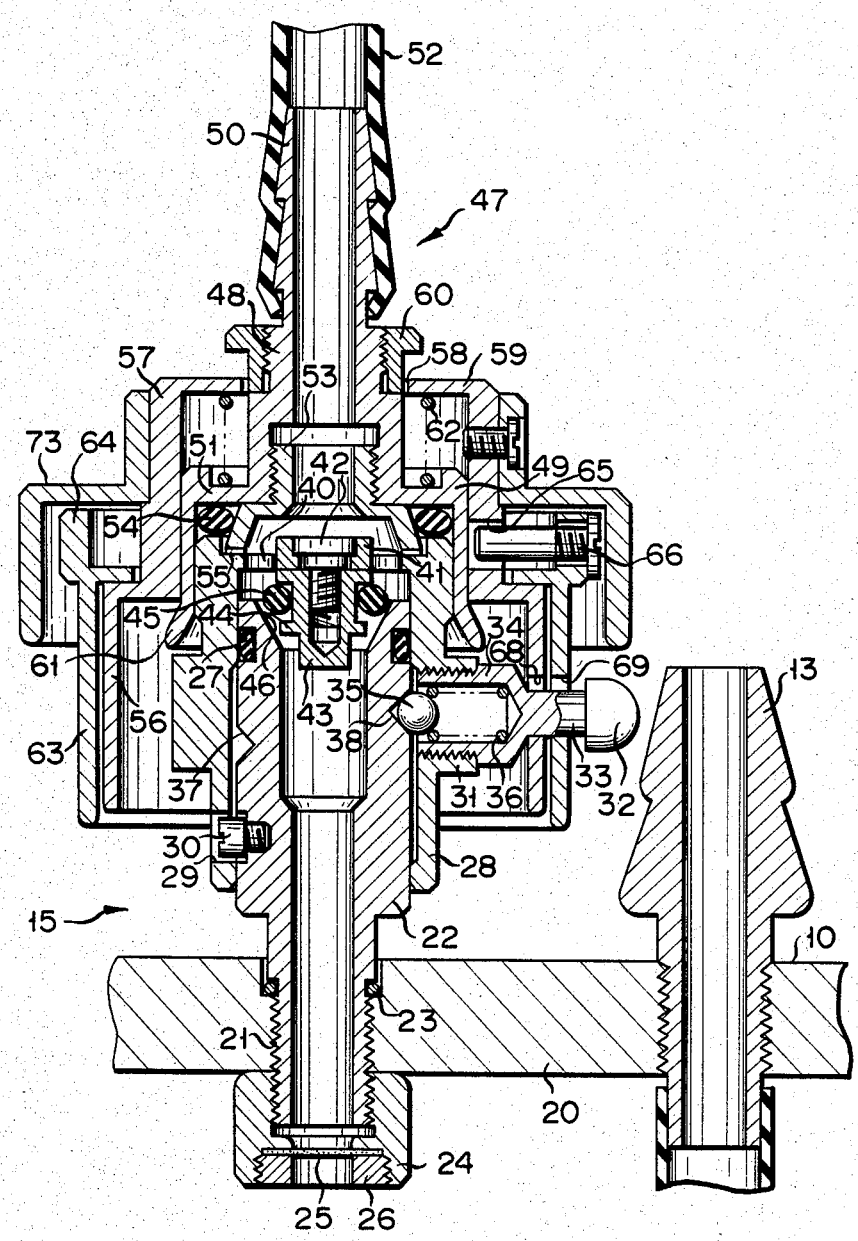
FIG. 5 is a side sectional view showing a state in which the supply connector is engagedly mounted on the communication portion.
Figure 7:
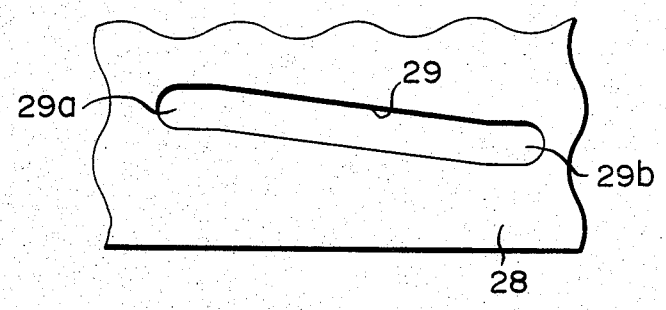
FIG. 7 shows a development of a cam slot in a cam cylinder of a communication portion.

A cam cylinder 28 is airtightly fitted on the outer peripheral surface of the projected outer end portion of the communication pipe 22 with the aid of a second O ring 27 for rotation and vertical motion. A cam slot 29 inclined at an angle to the axis of the cam cylinder 28, as shown in FIG. 7, is bored through the peripheral wall of the cam cylinder 28 within an angular range of about 180 degrees along the circumferential direction of the cam cylinder 28. The head portion of a cam pin 30 held in the communication pipe 22 is fitted in the cam slot 29. Also, as shown in FIG. 3, a tapped hole 31 is formed in the wall portion of the cam cylinder 28. The proximal end of a lever 32 constituting a retaining member (to be mentioned later) is screwed in the tapped hole 31. The lever 32 consists of a shaft portion 33 and a case portion 34 continuous therewith. The case portion 34 contains therein a spherical body 35 such as a steel ball. The spherical body 35 is urged by a spring 36 in a direction such that it projects from the inner peripheral surface of the cam cylinder 28 toward the outer peripheral surface of the communication pipe 22. Associated with the spherical body 35, first and second recesses 37 and 38 of a V-shaped cross-section are formed on the outer peripheral surface of the communication pipe 22 with a 180-degree relative circumferential deviation and some axial dislocation. The spherical body 35 elastically engages the recess 37 or 38 depending on the rotational position of the cam cylinder 28. Namely, the spherical body 35 engages the first recess 37 when the cam pin 30 is located on the top point 29a of the cam slot 29 so that the cam cylinder 28 is lowered relative to the communication pipe 22, as shown in FIG. 3. If the cam cylinder 28 is rotated 180 degrees from this position by means of the lever 32 so that the cam pin 30 is located on the bottom point 29b of the cam slot 29 to raise the cam cylinder 28, as shown in FIG. 5, then the spherical body 35 engages the second recess 38. Thus, the spherical body 35 and the first and second recesses 37 and 38 constitute a click mechanism for restricting the rotation of the cam cylinder 28.

Figure 4:
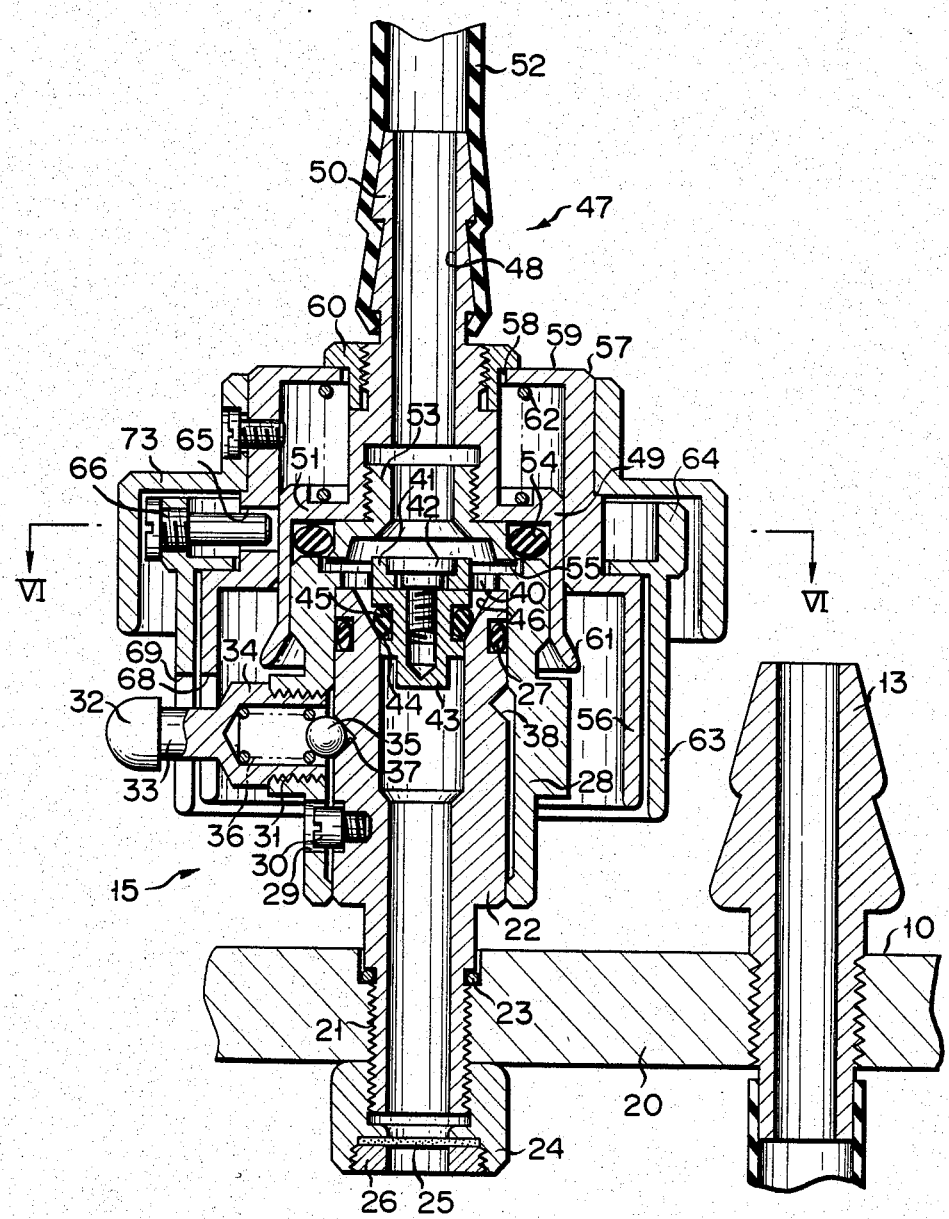
FIG. 4 is a side sectional view showing a state in which the supply connector is put on the communication portion.

A plurality of through holes 40 are bored through the peripheral portion of the upper end wall of the cam cylinder 28. A ring-shaped mounting portion 41 is formed at the central portion of the upper end wall. A retaining screw 42 is inserted in the mounting portion 41, and a valve plug 43 is screwed on the projected end portion of the retaining screw 42 inside the cam cylinder 22. A circumferential fitting groove 44 is cut in the outer peripheral suface of the valve plug 43, and is fitted with a third O ring 45 as an elastic member. When the cam cylinder 28 is lowered along the communication pipe 22, the third O ring 45 is pressed against a tapered valve seat 46 formed on the inner peripheral surface of the upper end portion of the communication pipe 22, thereby airtightly blocking up the communication pipe 22 in conjunction with the valve plug 43. Those members mentioned above constitute a valve mechanism in which the valve plug 43 opens and closes the communication pipe 22 as the cam cylinder 28 moves vertically. When the communication pipe 22 is closed by the valve plug 43, the lever 32 attached to the cam cylinder 28 is dislocated 180 degrees from the suction mouthpiece 13, as shown in FIG. 4. When the communication pipe 22 is opened by the valve plug 43, the extreme end of the lever 32 is located close to the suction mouthpiece 13, as shown in FIG. 5. In this state, therefore, it is impossible to connect the suction mouthpiece 13 with a suction hose (not shown). Thus, the lever 32 serves as a preventive member for preventing the normal use of the endoscope 1.

Figure 6:
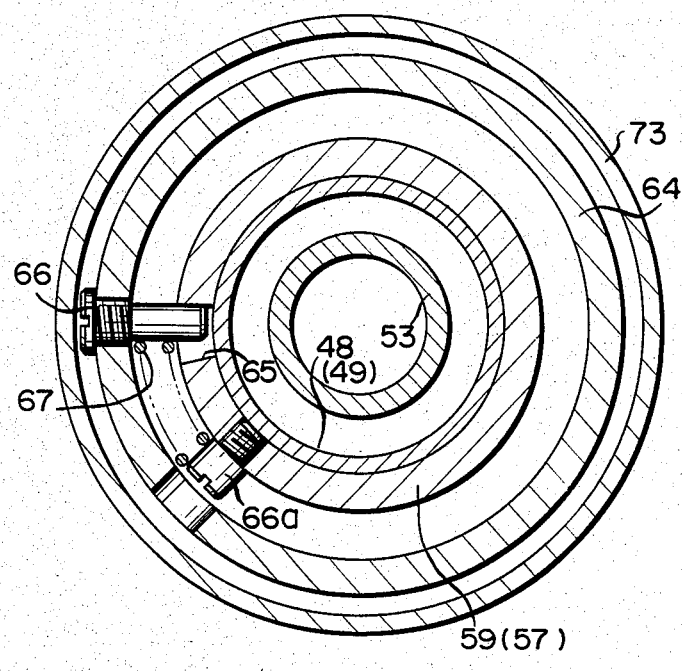
FIG. 6 is a sectional view taken along line VI—VI of FIG. 4.
Figure 8:
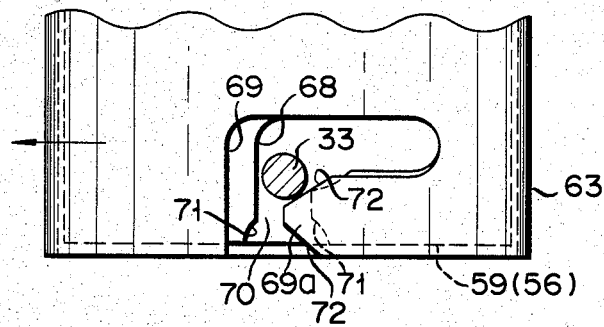
FIG. 8 is a side view showing engaging portions of the supply connector.

The communication portion 15 thus constructed on the side of the endoscope 1 is removably connected with a connector 47 for air supply. FIG. 3 shows a connecting mouthpiece 48. The connecting mouthpiece 48 is integrally formed of a thick portion 49 and a thin portion 50 which are connected by means of a stepped portion 51. The thin portion 50 is connected with a hose 52 of a supply line which communicates with an air source (not shown). The thick portion 49 is fitted on the outer peripheral surface of the cam cylinder 28 with a narrow gap between them. A presser cylinder 53 is screwed in the inner end edge of the thin portion 50 on the side of the stepped portion 51. A fourth O ring 54 is held between the outer surface of the outwardly expended peripheral wall of the presser cylinder 53 and the inner peripheral surface of the thick portion 49. The fourth O ring 54 is located to bear on the upper end face of the cam cylinder 28. The lower end face of the presser cylinder 53 is located to be brought close to the upper end face of the cam cylinder 28. A passage 55 is formed in the lower end face portion of the presser cylinder 53. A thin portion 57 of a first retaining cylinder 59 is put on the thick portion 49 of the connecting mouthpiece 48. Like the connecting mouthpiece 48, the retaining cylinder 59 has a thick portion 56 and the thin portion 57. The lower end face of the retaining cylinder 59 on the side of the thick portion 56 is opened, and a through hole 58 is bored through the central portion of the upper end face. The first retaining cylinder 59 can rotate and move up and down, and is prevented from slipping too far upward by a cap screw 60 fitted on the thin portion 50 of the connecting mouthpiece 48. Also, the first retaining cylinder 59 is prevented from slipping too far downward by a tapered wall 61 expended downward at the lower end portion of the thick portion 49 of the connecting mouthpiece 48. A spring 62 is interposed between the stepped portion 51 of the connecting mouthpiece 48 and the top end wall of the first retaining cylinder 59. A second retaining cylinder 63 is rotatably fitted on the outer peripheral surface of the thick portion 56 of the first retaining cylinder 59. A collar 64 surrounding the outer peripheral surface of the thin portion 57 of the first retaining cylinder 59 is formed on the peripheral edge of the upper end face of the second retaining cylinder 63. The collar 64 is fitted with a cam screw 66 whose tip end engages a cam hole 65 extending along the circumference of the thin portion 57 of the first retaining cylinder 59. Also, a retaining screw 66a is fitted in the thin portion 57 of the first retaining cylinder 59, dislocated at a predetermined circumferential angle from the cam hole 65, as shown in FIG. 6. A spring 67 is interposed between the retaining screw 66a and the cam screw 66. Thus, the first and second retaining cylinders 59 and 63 are urged to rotate in opposite directions by the restoring force of the spring 67. Also, as shown in FIG. 8, substantially inverted-L-shaped first and second engaging grooves 68 and 69 are formed in the thick portion 56 of the first retaining cylinder 59 and the peripheral wall of the second retaining cylinder 63, respectively, each having one end opening to the lower end face of each corresponding cylinder. The width of the open ends of the engaging grooves 68 and 69 is greater than the diameter of the shaft portion 33 of the lever 32. Since the first and second retaining cylinders 59 and 63 are urged in opposite directions by the spring 67, the open ends of their respective engaging grooves 68 and 69 are separated from each other, and the width of a gap 70 between the vertical side of the first engaging groove 68 and the tip end of a horizontal side 69a of the second engaging groove 69, is shorter than the diameter of the shaft portion 33. Arcuate surfaces 71 are formed on both sides of the open end of the first engaging groove 68, while slanted surfaces are formed on both sides of the tip end portion of the horizontal side 69a of the second engaging groove 69. Thus, the shaft portion 33 of the lever 32 can easily be led into the first and second engaging grooves 68 and 69. A cover 73 hanging over the second retaining cylinder 63 is fitted on the outer periphery of the thin portion 57 of the first retaining cylinder 59.

The operation of the aforementioned construction will now be described in detail. To supply air to the interior of the endoscope 1, the connector 47 is attached to the communication portion 15 with the communication pipe 22 closed by the valve plug 43, as shown in FIG. 4. Namely, the connector 47 is fitted into the communication portion 15 while aligning the open ends of the engaging grooves 68 and 69 of the first and second retaining cylinders 59 and 63 with the shaft portion 33 of the lever 32. Thereupon, the shaft portion 33 abuts against the arcuate surfaces 71 of the first retaining cylinder 59 and the lower slanted surface 72 of the second retaining cylinder 63, thereby rocking or rotating the retaining cylinders 59 and 63 in opposite directions against the restoring force of the spring 67 (FIG. 6). Thus, the gap 70 is widened to allow the shaft portion 33 to enter the first and second engaging grooves 68 and 69. When the shaft portion 33 enters the first and second engaging grooves 68 and 69, the first and second retaining cylinders 59 and 63 are rocked reversely by the restoring force of the spring 67 to narrow the gap 70. Thus, the shaft portion 33 cannot be easily disengaged from the first and second retaining cylinders 59 and 63.

After the connector 47 is attached to the communication portion 15 in this manner, the first and second retaining cylinders 59 and 63 of the connector 47 are rocked approximately 180 degrees in the direction of the arrow in FIG. 8. As a result, the shaft portion 33 of the lever 32 rocks or rotates with the connector 47, pushed by the closed end portions of the first and second engaging grooves 68 and 69. The cam cylinder 28 follows this rocking motion of the shaft portion 33. When the cam cylinder 28 rocks through approximately 180 degrees, the cam pin 30 engaging the cam slot 29 moves relative to the cam slot 29 from the top point 29a to the bottom point 29b thereof. Accordingly the cam cylinder 28 rises to cause the third O ring 45 on the valve plug 43 to be separated from the valve seat 46, thereby opening the communication pipe 22. Thus, air from the hose 52 connected to the connecting mouthpiece 48 is fed into the connector 10 through the communication pipe 22 to pressurize the interior of the endoscope 1, that is, the interior of the universal cord 4, the operating section 2, and the insertion section 3. If these members have pinholes or cracks, therefore, the endoscope 1 can be checked for leakage by immersing the members in water to detect air leaking from the endoscope 1. As the cam cylinder 28 rises, moreover, the connecting mouthpiece 48 also rises to compress the spring 62 between the stepped portion 51 and the top wall of the first retaining cylinder 59. Thereupon, the fourth O ring 54 is compressed between the stepped portion 51 and the upper end face of the cam cylinder 28 by the restoring force of the spring 62, so that air will never leak out from the area corresponding to these members. As the cam cylinder 28 is rocked 180 degrees from the position of FIG. 4 to the position of FIG. 5, the spherical body 35 in the case section 34 of the lever 32 is disengaged from the first recess 37, and elastically engages the second recess 38. Feeling such engagement, operator will know that the communication pipe 22 is open.

After the leakage check in water is completed in this manner, the air supply to the hose 52 is stopped, and then the supply connector 47 is rocked about 180 degrees in the direction opposite to the aforesaid direction. If the connector 47 is disengaged from the communication portion 15 when the spherical body 35 engages the first recess 37, the valve plug 43 is lowered together with the cam cylinder 28, as shown in FIG. 4, so that the communication pipe 22 is closed by the third O ring 45. While the open communication pipe 22 is being closed, the fourth O ring 54 is released from compression, so that the compressed air in the endoscope 1 is discharged to the outside through the passage 55 of the presser cylinder 53 and the space between the upper end face and outer peripheral surface of the cam cylinder 28 and the inner peripheral surface of the thick portion 49 of the connecting mouthpiece 48. Thus, the internal pressure of the endoscope 1 becomes equal to atmospheric pressure.

According to the endoscope 1 constructed in this manner, when the cam cylinder 28 is lowered relative to the communication pipe 22 so that the communication pipe 22 is closed by the valve plug 43, as shown in FIG. 4, the lever 32 is deviated about 180 degrees from the suction mouthpiece 13. In this state, therefore, the endoscope 1 can be used for observation or medical treatment inside the body cavity by connecting a suction hose to the suction mouthpiece 13.

When the valve plug 43 is raised so that the communication pipe 22 is open, however, the projected end of the lever 32 is located close to the suction mouthpiece 13, as shown in FIG. 5. Accordingly, it is impossible to connect the suction hose to the suction mouthpiece 13, so that the endoscope 1 cannot be used. In using the endoscope 1, therefore, it is essential to close the communication pipe 22 without fail. Thus, in disinfecting the endoscope 1 after use, it is impossible to allow a disinfectant to flow into the endoscope 1 with the communication pipe 22 open.

To attach the supply connector 47 to the communication portion 15, according to the aforementioned construction, the shaft portion 33 of the lever 32 attached to the communication portion 15 is fitted into the engaging grooves 68 and 69 of the first and second retaining cylinders 59 and 63 which are elastically displaced in the same direction against the restoring force of the spring 67. Thus, the engagement of the engaging grooves 68 and 69 and the lever 32 ensures the connection between the communication portion 15 and the supply connector 47. Accordingly, even if external force is applied to the supply connector 47 during the leakage check in water, the connector 47 will not be disengaged from the communication portion 15. Since the lever 32 can be elastically fitted in and disengaged from the engaging grooves 68 and 69 of the first and second retaining cylinders 59 and 63, the supply connector 47 can easily be attached to and detached from the communication portion 15. Also, the cam cylinder 28 is rocked or rotated by means of the lever 32 as the first and second retaining cylinders 59 and 63 rock. As the cam cylinder 28 rocks in this manner, the communication pipe 22 is opened or closed by the valve plug 43. Thus, the communication pipe 22 is opened and closed as the supply connector 47 is attached to and detached from the communication portion 15, so that the operating efficiency is improved, and the communication pipe 22 is prevented from being left open when the supply connector 47 is disengaged.

According to the aforementioned construction, moreover, the communication pipe 22 is opened and closed by the valve plug 43 which advances and retreats relative to the communication pipe 22 as the cam cylinder 28 rocks, and the valve seat 46 formed on the inner peripheral surface of the upper end of the communication pipe 22 against which the valve plug 43 abuts through the medium of the third O ring 45. In closing the communication pipe 22, the third O ring 45 is sandwiched between the valve plug 43 and the valve seat 46. Thus, the communication pipe 22 is securely closed by the third O ring 45, so that the liquid disinfectant will never penetrate to the interior of the endoscope 1 through the communication pipe 22. Moreover, the valve seat 46 is formed on the communication pipe 22, and the valve plug 43 is moved inside the communication pipe 22. Thus, the valve mechanism can be mounted more easily than the conventional valve mechanism in which the cock is connected to the communication pipe 22.

In disinfecting the endoscope 1 with the supply connector 47 disengaged from the communication portion 15, it is possible to immerse the endoscope 1 in the disinfectant without closing the communication pipe 22. In this event, the disinfectant enters the endoscope 1 through the communication pipe 22, but is checked and prevented from entering the connector 10 by the waterproof porous member 25 attached to the projected end portion of the communication pipe 22 inside the connector 10. Thus, the optical system and other elements in the endoscope 1 will never be damaged by the disinfectant. Although thin and fragile, the porous member 25 will never be broken by a sudden blow, since it is located inside the connector 10.

According to the aforementioned construction, moreover, the communication pipe 22 of the communication section 15 is opened and closed by means of the valve plug 43 which moves up and down as the cam cylinder 28 rotates. When the cam pipe 22 is closed by the valve plug 43, the spherical body 35 in the case portion 34 of the lever 32 is elastically engaged with the first recess 37 in the outer peripheral surface of the communication pipe 22. Even if external force is applied to the lever 32, the engagement of the spherical body 35 and the first recess 37 will make it difficult for the cam cylinder 28 to rock. In disinfecting the endoscope 1 in this state, therefore, the communication pipe 22 will be prevented from being easily opened to allow the penetration of the disinfectant into the endoscope 1. If the cam cylinder 28 is rocked to open the closed communication pipe 22, the spherical body 35 elastically engages the second recess 38. If the open communication pipe 22 is closed, on the other hand, the spherical body 35 elastically engages the first recess 37. By sensing this engagement, the operator can know that the communication pipe 22 has been opened or closed by the valve plug 43. Thus, the communication pipe 22 cannot readily be opened accidentally due to the use of the click mechanism consisting of the spherical body 35 and the first and second recesses 37 and 38. Moreover, the operating state of the communication pipe 22 can be easily checked by looking at the engagement of the spherical body 35 and the first or second recess 37 or 38.

Figure 9:
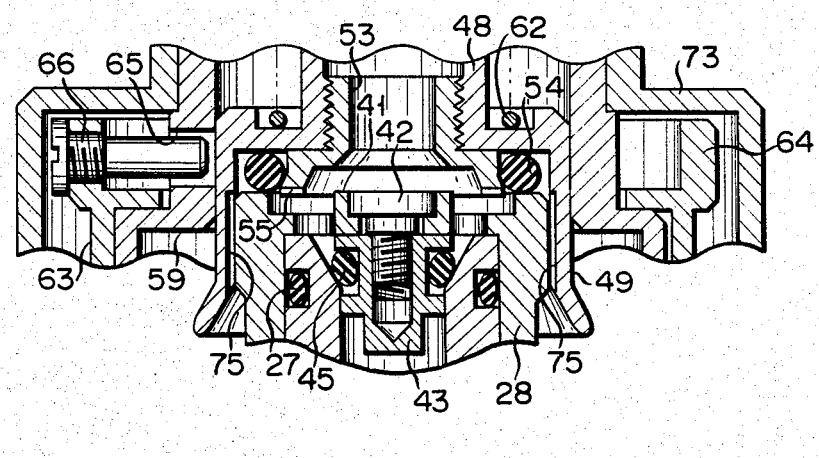
FIG. 9 is a sectional view showing a communication portion and a supply connector according to a second embodiment of the invention, which are connected to each other.
Figure 10:
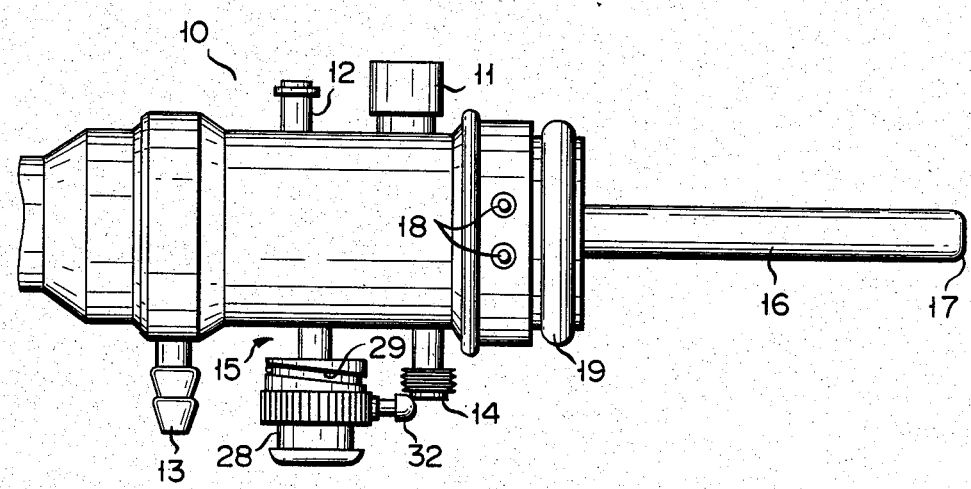
FIGS. 10 to 13 are side views showing endoscopes according to various other embodiments of the invention, each including a connector at the distal end of a universal cord of the endoscope.
Figure 11:
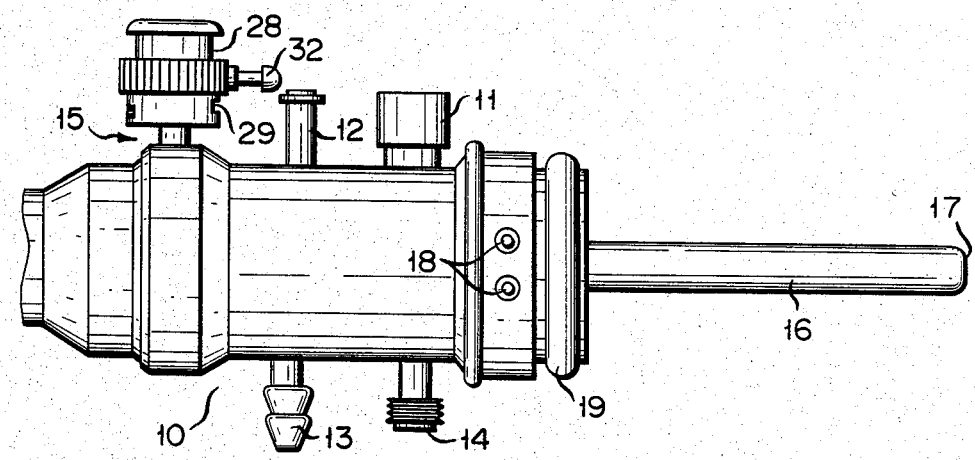
Figure 12:
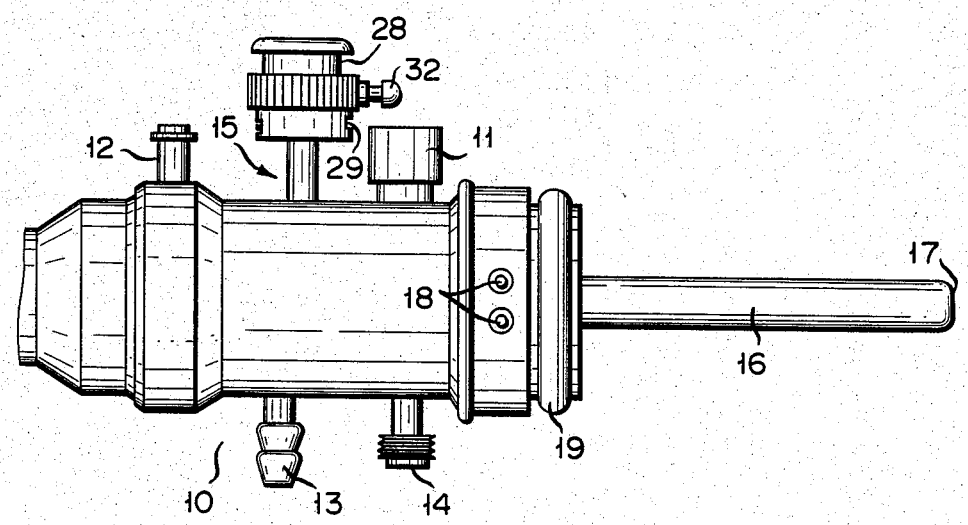
Figure 13:
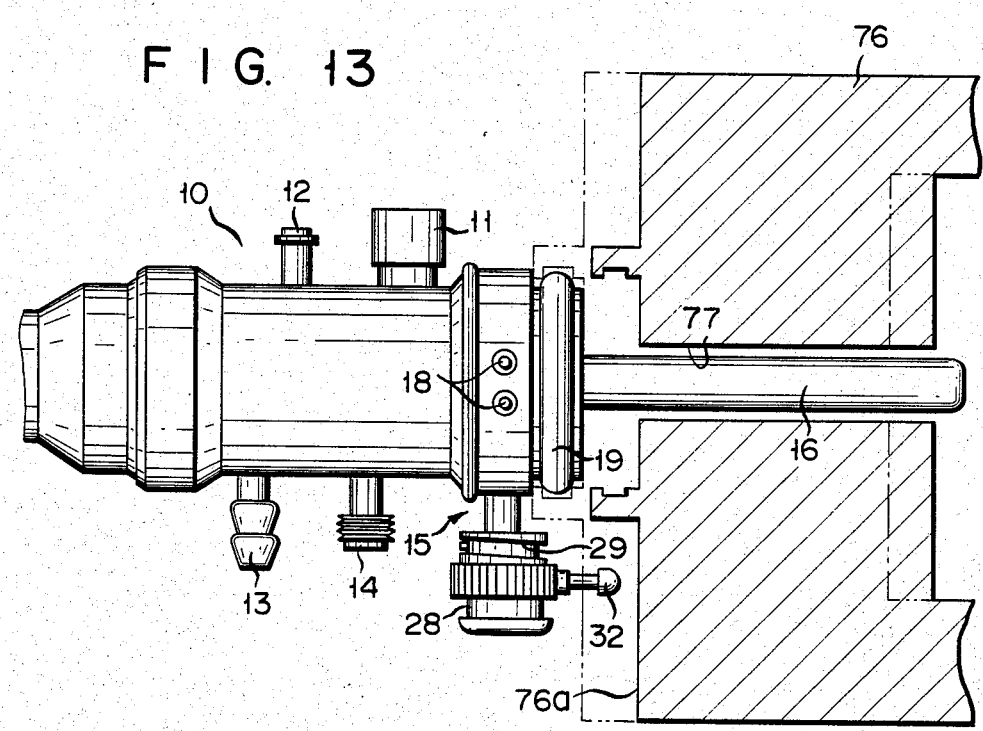

This invention is not limited to the embodiment described above. As shown in FIG. 9, for example, a plurality of grooves 75 opening to the lower end side of the connecting mouthpiece 48 may be formed on the inner peripheral surface of the thick portion 49 of the connecting mouthpiece 48. In this arrangement, compressed air inside the endoscope 1 can be positively discharged to the outside through the passage 55 of the presser cylinder 53 and the grooves 75 while the communication pipe 22 is being closed.

The communication portion 15 may be arranged as shown in FIGS. 10 to 13. In the embodiment shown in FIG. 10, the communication portion 15 is located close to the earth terminal 14 so that a lead wire (not shown) for grounding the endscope 1 when used with a high-frequency instrument cannot be connected to the earth terminal 14 while the communication portion 15 is open. In the embodiment shown in FIG. 11, the communication portion 15 is located close to the $CO_2$ mouthpiece 12 so that a $CO_2$ supply hose (not shown) cannot be connected to the $CO_2$ mouthpiece 12 while the communication portion 15 is open. In the embodiment shown in FIG. 12, the communication portion 15 is located close to the air/water mouthpiece 11 so that an air/water hose (not shown) cannot be connected to the air/water mouthpiece 11 while the communication portion 15 is open. In the embodiment shown in FIG. 13, the communication portion 15 is located at the end portion of the connector 10 so that, while the communication portion 15 is open, the extreme end portion 32 of the lever 32 projects beyond the end face of the connector 10, and abuts against the front 76a of a light source unit 76, thereby preventing the connector 10 from being securely inserted into a connecting socket 77 of the light source unit 76.

Thus, in all of the embodiments shown in FIGS. 10 to 13, the endoscope 1 cannot be used while the communication portion 15 is open. According to this arrangement, the cam portion 15 is always closed when the endoscope 1 is used, so that after use the endoscope 1 cannot be accidentally disinfected with the communication portion 15 open.

Instead of being fitted on the valve plug, a third O ring (not shown) may be fitted in an annular mounting groove formed on the valve seat.

Moreover, a porous member (not shown) may be supported at the middle portion of the communication pipe. It is only necessary that the porous member be disposed inside the communication portion so that it will not be broken by a shock.

What is claimed is:

1. A connector device for use in a system for checking air-leakage of an airtight endoscope, comprising:
   an endoscope including an airtight endoscope body, a communication port extending from the endoscope body and having a passage for communicating between the inside and the outside space of the endoscope body, a valve mechanism formed of a valve seat and a movable valve body and arranged in close proximity to the distal end of the port, for opening and closing the passage of the port, operating means for selectively opening and closing the valve mechanism, said operating means including a movable retaining member provided in the vicinity of the port;
   a supply connector adapted to be connected with the passage of the port in an airtight manner through said valve mechanism;
   a supply line for communicating through the supply connector to the passage of the port and into the interior of the endoscope body, for supplying air to detect air-leakage between the inside and the outside space of the endoscope body; and
   a retaining mechanism attached to the supply connector and adapted to communicate with the valve mechanism and engage the retaining member wherein the supply connector is removably held on the communication port by operation of the retaining member.

2. The connector device according to claim 1, wherein said operating means is operative to open the valve mechanism when the retaining mechanism engages the retaining member and said retaining member is operated.

3. The connector device according to claim 1, wherein said retaining member is a lever for controlling the operating means.

4. The connector device according to claim 1, wherein said operating means includes a blocking member for preventing normal use of the endoscope when the valve mechanism is opened.

5. The connector device according to claim 4, wherein said blocking member is formed by a part of said retaining member.

6. The connector device according to claim 1, further including a porous member interposed between the communication port and the interior of the endoscope body, said porous member being impervious to a liquid and permeable to air.

7. The connector device according to claim 1, wherein said valve mechanism includes an elastic member associated with one of the valve seat and the valve body and adapted to be interposed between the valve seat and the valve body to seal the passage of the valve port when the valve mechanism is closed.

8. The connector device according to claim 1, wherein said operating means includes a click mechanism for regulating operating end positions of the operating means of the valve mechanism.

* * * * *